United States Patent [19]

Clark

[11] 4,005,191
[45] Jan. 25, 1977

[54] TOPICAL OINTMENT COMPOSITION

[76] Inventor: Mary G. Clark, 121 W. Grace St., Old Forge, Pa. 18518

[22] Filed: Nov. 5, 1975

[21] Appl. No.: 628,972

Related U.S. Application Data

[63] Continuation of Ser. No. 476,294, June 4, 1974, abandoned.

[52] U.S. Cl. .............................. 424/154; 424/156; 424/157
[51] Int. Cl.² ....................................... A61K 33/06
[58] Field of Search .................. 424/154, 156, 157

[56] References Cited

UNITED STATES PATENTS

| 139,315 | 5/1873 | Hucks | 424/157 |
|---|---|---|---|
| 1,375,220 | 4/1921 | Leist | 424/156 |
| 1,999,161 | 4/1935 | Walton | 424/157 |
| 3,137,622 | 6/1964 | Mueller et al. | 424/157 |
| 3,265,571 | 8/1966 | Krezanoski | 424/157 |

OTHER PUBLICATIONS

Sagarin, Cosmetics, Science and Technology, (1957), pp. 1163–1164.
Physician's Desk Reference, (PDR), (1971), p. 674.
Husa's Pharmaceutical Dispensing, (1966), pp. 144–151.
Handbook of Non-Prescription Drugs, (1973), pp. 145–146.

*Primary Examiner*—Norman A. Drezin
*Attorney, Agent, or Firm*—Watson, Cole, Grindle & Watson

[57] ABSTRACT

A topical ointment composition is provided which includes a mixture of non-systemic bases comprising calcium carbonate, magnesium hydroxide, and aluminum hydroxide. The composition also includes an anhydrous lanolin base carrier material and a hydrophilic ointment base carrier material, and the ointment composition is effective to essentially adjust the acid-base balance at the area of topical application to a point which corresponds with normal healthy body tissue. The composition may further include a compound having pharmaceutically acceptable anesthetic properties. In addition to the topical ointment composition, a method is provided for treating skin injuries involving inflammation or destruction of tissue, such as decubitus ulcers, varicose ulcers and burns, which method involves preparing the above noted composition and applying it to the affected area.

13 Claims, No Drawings

TOPICAL OINTMENT COMPOSITION

This is a continuation of copending application Ser. No. 476,294, filed June 4, 1974, now abandoned.

BACKGROUND OF THE INVENTION

1. Field of the Invention

This invention relates to the direct treatment of injured mammalian tissue, for example, abraded, lacerated or ulcerated tissues, through the use of a topical ointment composition which has the capacity of adjusting the acid-base balance of the area to which the composition is applied to a point where healing from within can take place.

2. Prior Observations

The skin, supporting body tissues, connective tissues and viscera are subject to a variety of irritations, infections and injuries. These often result in the disruption of the continuity, configuration and appearance of normal tissues and may appear as areas of ulceration, necrosis, contusion, laceration, inflammation and tumefaction. Conventional compositions for dressings to be applied to such irritated or injured tissues often act as foreign bodies and are frequently themselves a source of irritation which may impede the healing process and promote infection.

The skin is composed of two layers, i.e., the epidermis or cuticle and the dermis or true skin. The epidermis is a thin outer layer composed of stratified epithelium. The cells in the deepest portion of the epidermis, the Malpighian layer, multiply and, in growing, push the older cells of the epidermis upward toward the surface. As these cells move upwardly they become flattened and plate-like in shape. The epidermis, being generally devoid of blood vessels, is dependent for its nutrition upon the vessels found in the dermis. These vessels end as capilliary loops in the papillae of the dermis. The more superficial cells of the epidermis, being far removed from the nutrient supply, gradually degenerate and their proteins are transformed into keratin. This process, termed keratinization, results in the death of the cells. Keratin is the most insoluble of all proteinaceous material which gives the upper layer of the skin (the stratum corneum) a horn like consistency. During the life process, the outermost dead scales of keratin are gradually shed and replaced by more recently keratinized cells. Keratin also is found in the appendages of the skin, that is, in the nails and hair. In the lower animals it is found in the horns, hoofs and claws. In the palms of the hands and soles of the feet, the epidermis is much thicker than elsewhere.

The true skin, corium or dermis, lies just below the Malpighian layer and is formed of loose connective tissue which sends little elevations known as papillae into the cuticle or epidermis. At its deepest portions the dermis gradually passes into the areolar subcutaneous tissue. In the dermis, or more especially, in the subcutaneous tissue, a variable amount of adipose tissue exists. While the epidermis is not supplied with blood vessels, the dermis is very vascular and the sebaceous (oil) and sudoriferous (sweat) glands are located in the dermis. The oil glands, which reside in the deeper parts of the skin, are distributed in all areas of the body except the soles of the feet and the palms of the hands. The sebaceous secretion, known as sebum, contains fats, proteins, water, salt, and remnants of epithelial cells. The sebum protects the structures of the skin and the hair against intolerable drying and breakage by oiling the same and thus the physical integrity of the skin is preserved. Additionally, the sebum prevents excessive loss of water by the skin.

One of the primary functions of the skin is protection. The epidermis of the skin, which is composed of hard, resistant cells, forms the bodies first line of defense against mechanical and chemical injuries and, above all, against bacterial invasion, because the unbroken skin is substantially germ proof. This protection is evidenced by the frequent infections which occur when the skin is injured so as to expose the underlying tissues. Recently, it has been demonstrated that the skin not only serves as a mechanical barrier but that it also possesses immunizing powers. Additionally, the sense organs for heat and cold, touch and pain are located in the dermis. Further, the skin helps to regulate body temperature through vasomotor reactions of blood vessels and through evaporation of perspiration. Perspiration sometimes has acidic and sometimes basic properties and its odor may be very marked and differs in various regions of the body. The skin also plays an important part in water metabolism, calcium metabolism and to a lesser degree, excretion and adsorption.

Various injuries which effect the skin include those caused by allergic reactions, mechanical impact or abrasion, chemical attack, heat, etc. These may result in disruption of normal tissue continuity, configuration and appearance and may appear as areas of ulceration, necrosis, contusion, laceration, inflammation and tumefaction.

The terms above, for the purposes of this specification, are intended to have the following meanings:

Ulcer — is a local defect or excavation of the surfaces of an organ produced by sloughing of necrotic inflammatory tissue;

Decubitus ulcer — is an ulceration caused by prolonged pressure on a body area in a patient confined to bed;

Necrosis — is the death of a cell as a result of a disease or injury;

Contusion — is an injury to tissues without breakage of the skin;

Laceration — is a wound produced by tearing;

Inflammation — is a specific tissue response to injury by living agents, or to electrical, chemical or mechanical trauma, evidenced by vascular dilatation, fluid exudation, or accumulation of lukocytes or any combination of the three;

Tumefaction — is a swelling or puffiness;

Rash — is a temporary erruption on the skin;

Diaper Rash — is a dermatitis of the gluteal region of infants.

Erythema — is a congestive or exudative redness of the skin caused by hyperima which is an excess of blood in a particular part;

Edema — is an abnormal accumulation of fluid in the intracellular spaces of the body;

Eczema — is generally a skin disease having associated therewith, itching and redness.

Various compositions useful for treatment of injuries to the skin are known in the prior art. Among these known compositions are the following:

Furacin (a registered trademark of Eaton Laboratory, Norwich, New York) is a topical cream containing nitrofurazone in a base consisting of glycerine, cetyl alcohol, mineral oil, an ethoxylated fatty alcohol, methylparaben, propylparaben and water. The water miscible base is self-emulsifying in various body fluids. The topical cream finds use in the treatment or prophylaxis of the surface bacterial infections.

Elase Ointment (a registered trademark of the Parke-Davis Company, Detroit, Michigan) is a combination of two lytic enzymes, fibrinolysin and desoxyribonuclease, in an ointment. The fibrinolysin component is derived from bovine plasma and the desoxyribonuclease is isolated in a purified form from bovine pancreas. The combination of these two enzymes is based on the observation that purulent exudates consist largely of fibrinous material and nucleoprotein. Desoxyribonuclease attacks the desoxyribonucleic acid (DNA) and fibrinolysin attacks principally fibrin of blood clots and fibrinous exudates. Elase is used topically as a debriding agent in a variety of inflammatory and infected lesions including (1) general surgical wounds, (2) ulcerative lesions, i.e., trophic, decubitus, stasis, arteriosclerotic; and (3) second and third degree burns.

Oxylone (a registered trademark of the Upjohn Company, Kalamazoo, Michigan) contains fluorometholone, which is a steroid, in addition to glyceryl monostearate, spermaceti, polyethylene glycol emulsifier, water and preservatives. This material includes a water soluble vanishing cream base designed for use on exposed regions of the skin such as the face and hands and is allegedly effective because of the anti-inflammatory, anti-pruritic and vasoconstrictive action provided by the steroid, fluorometholone. The cream is used to obtain symptomatic relief and adjunctive management of various dermatoses including sunburn, eczema and diaper rash.

Mycolog (a registered trademark of E. R. Squibb & Sons, Princeton, New Jersey) is a dermatologic preparation used in cases of dermatitis complicated with a superficial bacterial infection. Among other things, it is anti-fungal and anti-bacterial and contains nystatin, neomycin sulfate, gramicidin, and triamcinolone acetonide either in a vanishing cream base or in a protective base of polyethylene and mineral oil gel.

Neosporin (a registered trademark of the Burroughs-Wellcome Company, North Carolina) provides antibacterial action against commonly occuring bacteria known to be topical invaders. The ointment contains neomycin sulfate, zinc bacitracin and polymyxin B-sulfate.

The foregoing compositions, even though many of the same include fungicides, bacteriacides or hazardous steroids, still do not provide either the degree or speed of healing which is obtained with the composition of the instant invention in the treatment of many injuries to the skin, as will be clearly shown in the examples infra.

SUMMARY OF THE INVENTION

It is a principal object of the instant invention to provide a topical ointment composition useful for treating injuries to the skin which result in ulcerated, lacerated or abraded tissue. In this connection it is a principal aim of the invention to provide a method for producing such a composition.

It is a further object of the present invention to provide a filling or cementing material for injured tissue which is soft, flexible, protective and non-irritating and which provides a temporary nucleus to facilitate the growth of replacement tissues for healing purposes.

Other objects and advantages of the present invention including stability, convenience, economy and adaptability for use in conjunction with various known materials will be apparent from the following detailed description of the preferred embodiments thereof.

Briefly, the composition of the instant invention is useful in treating various injuries to the skin which result in ulcerated, lacerated or abraded tissue and in particular the composition is useful in the treatment of decubitus ulcers. The composition is in the form of a topical ointment and contains a mixture of non-systemic bases, a lanolin base carrier material and a hydrophilic ointment carrier material. The mixture of bases is present in the composition in an amount effective to adjust the acid-base balance of the area of topical application to a point which corresponds with normal, healthy body tissue. Optionally the topical ointment may also include a compound having anesthetic properties.

More specifically, the mixture of non-systemic bases consists essentially of from about 7 to about 82 weight percent calcium carbonate, from about 5 to about 77 weight percent magnesium hydroxide and from about 6 to about 80 weight percent aluminum hydroxide and the percentages of these enumerated bases total approximately 100 percent of the mixture thereof. Moreover, the weight ratio of the anhydrous lanolin base carrier material to the hydrophilic ointment base carrier material in the composition ranges from approximately 2:1 to approximately 1:2. Additionally, the weight ratio of base carrier materials to non-systemic bases in said composition should be in the range of about 21:1 to 213:1 to achieve the best results. The compound having anesthetic properties may be, for example, dibucaine, benzocaine, lidocaine, pramoxine hydrochloride, etc. However, dibucaine is preferred.

Additionally, the instant invention provides a method for preparing such a topical ointment composition which comprises forming a paste comprising a mixture of non-systemic bases including calcium carbonate, magnesium hydroxide and aluminum hydroxide and a sufficient amount of water to provide a smooth, moist paste and separately admixing an anhydrous lanolin base carrier material and a hydrophilic ointment base carrier material in a weight ratio ranging from approximately 2:1 to approximately 1:2. Thereafter the admixture of base carrier materials is blended with the paste to obtain a workable homogeneous paste.

DETAILED DESCRIPTION OF THE PREFERRED EMBODIMENTS OF THE INVENTION

In the preferred embodiment of the invention, a mixture of non-systemic bases consisting essentially of about 7 to about 82 weight percent calcium carbonate, from about 5 to about 77 weight percent magnesium hydroxide and from about 6 to about 80 weight percent aluminum hydroxide is provided. The percentages of the components in the mixture total approximately 100 percent thereof and a sufficient amount of water is added to the mixture to provide a smooth, moist paste which preferably has a pH in the range of from about 8.0 to about 9.5. An anhydrous lanolin base carrier material and a hydrophilic ointment base carrier material are admixed in a weight ratio ranging from approximately 2:1 to approximately 1:2 and the mixture of bases is blended with the admixture of base carrier materials. The blended composition contains an amount of the basic paste effective to essentially adjust the acid-base balance at the area of topical application to a point which corresponds with normal, healthy body tissue and in this connection, the weight ratio of base carrier materials to nonsystemic bases in said composition should preferably be in the range of from about 21:1 to about 213:1.

More preferably the admixture of bases contains from about 25 to about 50 weight percent of each of the enumerated compounds and the composition contains substantially equal quantities of the base carrier materials. Most preferably the composition contains the following ingredients in the indicated proportions:

| | |
|---|---|
| Calcium carbonate | 250 mg |
| Magnesium Hydroxide | 200 mg |
| Aluminum Hydroxide | 225 mg |
| Dibucaine (1% in Petrolatum*) | 150 mg |
| Anhydrous lanolin | 28.35 gms |
| Hydrophilic Ointment | 28.35 gms |
| *Petrolatum | 15 gms |
| Water | 10 cc |

In mixing the above ingredients to yield a topical ointment, the calcium carbonate, magnesium hydroxide, and aluminum hydroxide are first mixed with water with the water being added a little bit at a time to form a smooth moist mixture having a paste-like consistency and which contains approximately 37 weight percent calcium carbonate, 29.7 weight percent magnesium hydroxide and 33.3 weight percent aluminum hydroxide. Dibucaine in a petrolatum base is then added while mixing continuously to maintain a homogenous paste-like consistency. The paste containing the systemic bases and the anesthetic just formed is then added to a homogenous mixture of the anhydrous lanolin and the hydrophilic ointment with continuous mixing to insure homogeneity. The composition thus prepared has a weight ratio of base carrier materials to nonsystemic bases of about 106:1 since the petrolatum carrier for the dibucaine may generally be classified as a hydrophobic ointment. If the dibucaine is not included, then the ratio of base carrier materials to non-systemic bases would be about 84:1.

When the composition is applied topically, the calcium carbonate and the magnesium hydroxide provide a rapid neutralization of the area under treatment, while the aluminum hydroxide provides a slower but longer lasting neutralization in addition to a mild astringent effect. The dibucaine is used essentially for its anesthetic or analgesic effect, i.e., as a topical anesthetic. The anhydrous lanolin and the hydrophilic ointment provide a carrier base which facilitates application of the composition to topical areas, assists in maintaining the compound in a semi-solid homogeneous paste-like consistency, and enhances lubrication and absorption by the skin.

The non-systemic bases which make up a portion of the topical ointment of the instant invention are all readily available compounds. Calcium carbonate ($CaCO_3$) is a white powder or colorless crystal having virtually no odor and no taste. It is insoluble in water and alcohol but soluble in acids with the evolution of carbon dioxide.

Magnesium hydroxide ($Mg(OH)_2$), also known as milk of magnesia, magnesia or magma, is a white powder having no odor, is soluble in solutions of ammonium salts and dilute acids, and is insoluble in water and alcohol.

Aluminum hydroxide ($Al_2O_3 \cdot 3H_2O$ or $Al(OH)_3$), also known as aluminum trihydrate, aluminum hydrate, hydrated alumina or hydrated aluminum oxide, generally exists in the form of a white crystalline powder, granules or balls. It is insoluble in water and soluble in mineral acids and caustic soda.

Dibucaine hydrochloride (2-butoxy-N-(2-diethylaminoethyl) cinchoninamide hydrochloride), can be prepared by a process disclosed in U.S. Pat. No. 1,825,623. The dibucaine hydrochloride is incorporated at a concentration of about 0.5 to about 2%, preferably about 1%, in a carrier which is preferably petrolatum but can also be a cream or an oil which is pharmaceutically acceptable for topical application.

Anhydrous lanolin is the purified wool fat of sheep which consists of cholesteryl and isocholesteryl esters of higher fatty acids. The preparation of esterified or so called modified lanolins which are clearly soluble in mineral oils is described by Conrad and Motiuk in U.S. Pat. No. 2,725,334. The compound itself is a tenacious, semi-solid fat having a very slight odor and which melts at between 38° and 42° C. It is insoluble in water but will mix with water without separation in a ratio of about 2 parts water to 1 part lanolin. Lanolin is a neutral, tenacious, non-irritating, non-volatile base for ointments and creams which is more rapidly absorbed by the skin than most other ointment bases. The difference between anhydrous lanolin and lanolin is that ordinary lanolin, which is hydrous wool fat, contains between 25 and 30% water. Since it has been found in the course of experimentation with the composition of the instant invention that water is not advantageous to the healing process, that is, it does not freely promote but rather hinders the healing process, it is preferred to use the anhydrous lanolin. It should also be noted at this point that in preparation of the composition, only enough water is used to provide a smooth homogeneous paste of the non-systemic bases prior to admixing the latter with the anhydrous lanolin and the hydrophilic ointment. Only enough water should be used in the composition to maintain the same in a paste-like consistency to facilitate the topical application thereof.

A hydrophilic ointment is an ointment which has an affinity for water, that is, the same is capable of uniting with or dissolving in water. Such ointment can be made of any suitable composition which can be utilized as a carrier material for the active constituents of the composition. Generally, these ointments have a mineral oil or petrolatum base and may optionally contain surfactants to assist in maintaining and forming homogeneous mixtures. Petrolatum, a paraffin jelly commonly referred to as Vaseline (a registered trademark of the Vick Company), is a purified mixture of semi-solid hydrocarbons, chiefly of the methane series. The compound is yellowish to light amber or white in color and comprises a semi-solid, unctuous mass which has virtually no odor and no taste. It melts at approximately 38° to 54° C and is insoluble in water and alcohol. It is used generally as an ointment base, as a lubricant or as a protective dressing.

The method of treating injuries to the skin utilizing the composition of the instant invention involves first thoroughly cleaning the wound, or the specifically affected area, with an antiseptic. Many antiseptics will do, however, in the process of the instant invention, hydrogen peroxide (3%) is preferred. After such cleansing, the wound is then rinsed thoroughly with an abundance of preferably luke warm water. The affected area is then dried thoroughly and cleansed with a sterile absorbent, such as cotton swabs or gauze pads to remove as much moisture as possible. The affected area, such as the ulcer crater, is then generously packed with the topical ointment composition and covered with a sterile dressing. The procedure is repeated as required, generally about every 12 hours. After each application, when removing the dressing to reapply the ointment, the ointment applied will have caked and can generally be removed from the ulcer crater in bulk form.

Various additives, modifiers, or selected therapeutic substances may be added to the instant composition with the proviso that they are not added in amounts such that the effectiveness of the inventive composition is hindered or to such a degree that the composition becomes pharmaceutically unacceptable.

Various preferred forms of the topical ointment composition of the present invention are described in the following examples:

EXAMPLE I

The following constituents were mixed to provide an example of the instant composition:

| | |
|---|---|
| Calcium carbonate | 250 mg |
| Magnesium Hydroxide | 200 mg |
| Aluminum Hydroxide | 225 mg |
| Dibucaine (1% in petrolatum*) | 100 mg |
| Anhydrous Lanolin | 28.35 gm |
| Hydrophilic Ointment | 28.35 gm |
| *Petrolatum | 10 gm |
| Water | 5 cc |

The calcium carbonate, magnesium hydroxide, and the aluminum hydroxide are substantially insoluble in water. To assist in the dispersion of these components in the base carrier material, a paste was formed therefrom by adding a little water at a time to form a relatively homogeneous dispersion thereof. The dibucaine (1%), which is provided in a petrolatum base, was then added with mixing to obtain a smooth homogeneous mixture. The anhydrous lanolin and the hydrophilic ointment were then mixed to provide a homogeneous composition which was blended with the dispersion of the calcium carbonate, the magnesium hydroxide, the aluminum hydroxide and the dibucaine. The entire composition was mixed thoroughly to insure a homogeneous dispersion of all of the ingredients.

The calcium carbonate and the magnesium hydroxide provide a relatively rapid neutralization of the area under treatment. The aluminum hydroxide, however, provides a slower longer lasting neutralization in addition to a mild astringent effect. The 1% dibucaine hydrochloride dispersed in petrolatum is used for its analgesic or anesthetic effect and the amount may be varied to increase or decrease the anesthetic effect depending on the condition being treated. The anhydrous lanolin and the hydrophilic ointment are utilized to provide a base for the composition which facilitates its application and retention in the area of treatment.

EXAMPLE II

A patient was discharged from a hospital after a three week stay during which the patient had developed two large decubitus ulcers on the right buttock. The ulcers were each approximately three-quarters of an inch deep, were conical in shape, had a strong displeasing odor and a serous exudate and exhibited some gangrenous tissue around the edges of the normal skin. This patient was treated for three or four months with various known topical creams or ointments of the type generally used to treat this type of lesion. These topical creams and ointments included Furacin, Elase ointment, Oxylone cream, Mycolog and Neosporin. During the course of the treatment with the foregoing ointments there was no apparent improvement in the condition. In fact, the condition worsened and the patient was advised to make arrangements for skin grafting. Prior to the grafting it was suggested that the patient utilize the ointment of the present invention which composition in this instance was as follows: (prepared in accordance with the method of Example I)

| | |
|---|---|
| Calcium Carbonate | 250 mg |
| Magnesium Hydroxide | 200 mg |
| Aluminum Hydroxide | 225 mg |
| Dibucaine (1% in Petrolatum*) | 150 mg |
| Anhydrous Lanolin | 28.35 gm |
| Hydrophilic Ointment | 28.35 gm |
| *Petrolatum | 15 gm |
| Water | 10 cc |

The specific method of treatment using the topical ointment composition noted above involved first cleansing each crater with a solution of hydrogen peroxide (3%) and thereafter washing the same with a large volume of luke warm water followed by drying thoroughly with a soft absorbent material such as cotton or gauze to remove exudate and any necrotic tissue. The ulcer craters were then packed thoroughly with the topical ointment composition prepared above and were covered with gauze pads. The patient was advised to reapply the ointment with a new dressing at approximately 12 hour intervals. After the first 12 hour period the dressing was removed and it was found that the ointment had solidified such that the same could be removed from each ulcer crater in a dry solid mass. The procedure was repeated and healthy pink tissue was observed in the ulcer craters within 48 hours after the first treatment with the topical ointment composition. It was noted during the treatment that the use of any outside aqueous compositions, such as soap or plain water, considerably retarded healing and enhanced irritation. The ulcer craters were essentially completely healed in four (4) weeks with virtually no scar tissue. It was also noted during the treatment of the decubitus ulcers that the wound did not require cleansing during the period of treatment, that is, the topical ointment composition of the instant invention acted effectively as a cleansing agent and no other external agents were required during treatment to maintain the wound or the injured tissue in a cleansed state.

EXAMPLE III

A male construction worker who had suffered from chronic contact dermatitis for 8 to 9 years due to constant exposure to varying conditions of weather, experienced dry, cracked areas and scaling of the epidermis accompanied by some throbbing and partial loss of feeling. The patient was advised to clean his hands with a paste comprising a suspension of 250 mg of calcium carbonate, 200 mg of magnesium hydroxide and 225 mg of aluminum hydroxide in 10 cc of water, followed by rinsing with lukewarm water and thorough drying. The following ointment composition, prepared in accordance with the procedure outlined in Example I above, was then applied to the affected areas every 12 hours:

| | |
|---|---|
| Calcium Carbonate | 1,000 mg |
| Magnesium Hydroxide | 800 mg |
| Aluminum Hydroxide | 900 mg |
| Dibucaine Hydrochloride (1% in Petrolatum*) | 600 mg |
| Anhydrous Lanolin | 28.35 gm |
| Hydrophilic Ointment | 28.35 gm |
| Water | 40 cc |
| *Petrolatum | 60 gm |

After one week of continued therapy using this composition, the previously dried, cracked and scaling areas of the epidermis were clean and smooth and there was a complete absence of scaling. In addition the throbbing had been relieved and the sense of touch had been renewed.

EXAMPLE IV

In this instance, a patient suffering from an acute, chemically induced, allergic contact dermatitis experienced pruritus, edema, erythema and pain. The areas of the epidermis involved were the cheeks, where scaling, edema and pruritus were noted, and the eyelids where cracking occurred along the outer corners of the eyes. The patient was unable to open his eyelids without severe pulling and pain in the corners of each eye. The composition of Example III was applied initially, after which the patient noted an immediate cooling effect and a loss of pain and was able to open his eyelids all of the way shortly after the first treatment. The treatment was continued using the formula of Example III for three (3) days after which time the patient was seen again. The skin at this time was smooth and the edema had subsided; however, a slight bit of redness was still present. The patient was given a modified formula similar to the composition of Example III except for a 66% reduction in the concentration of the dibucaine hydrochloride to reduce any irritation which might have been caused thereby. After four days of treatment with such modified topical ointment composition of the instant invention, all symptoms had subsided and the affected areas appeared normal.

EXAMPLE V

In this instance, a patient suffering from contact dermatitis of the lower extremities, manifested by itching and redness, was treated for one (1) week with the following topical ointment composition which was prepared in accordance with the method of Example I:

| | |
|---|---|
| Calcium Carbonate | 250 mg |
| Magnesium Hydroxide | 200 mg |
| Aluminum Hydroxide | 225 mg |
| Dibucaine Hydrochloride (1% in petrolatum*) | 300 mg |
| Anhydrous Lanolin | 28.35 gm |
| Hydrophilic Ointment | 28.35 gm |
| *Petrolatum | 30 gm |
| Water | 10 cc |

The patient was instructed carefully regarding the correct procedure as to treatment of the dermatitis, i.e., cleansing the affected area and allowing it to dry thoroughly prior to the application of the ointment. The patient was also directed to use no soap and to cleanse the affected area with the antiacid composition noted in Example III, followed by rinsing with warm water and thorough drying prior to application of the ointment. Within 48 hours the itching and redness had subsided.

EXAMPLE VI

The composition described in Example II was used to treat diaper rashes of varying severity using the procedure for application outlined above. The condition in all cases was considerably improved, if not totally cured, after multiple applications of the topical ointment composition. The ointment applied to the genitorectal areas apparently forms a protective film over the skin and tends to neutralize the acidity of the urine prior to its coming into contact with the epidermis. Similarly, results were noted in cases of vaginitis and/or pruritis vulvae where the condition was considerably alleviated, if not cured completely, by application of the ointment of Example II to the affected areas. Preapplication of the antiacid suspension was not necessary as in some of the previous Examples.

EXAMPLE VII

A patient suffering from herpes simplex indicated by dry cracked lips and drying of the nasal mucosa with patches of erythema along the outer edge of the nostrils was treated with the topical ointment of the present invention. Repeated application of the topical ointment composition described in Example II resulted in a complete healing of the affected area.

EXAMPLE VIII

In this case, the patient had received first, second and third degree burns on the left leg extending from the mid-calf to the upper thigh. During a 3 to 4 week hospital stay the patient was treated with whirlpool baths and Furacin ointment and little or no improvement was observed. Upon discharge from the hospital, the burned area was generally raw with some slight scab formation and had a serous exudate emerging from the raw areas. In addition, four of the largest burned areas exhibited some gangrenous tissue around the edges. The affected area was cleansed thoroughly with a lukewarm solution of 3% hydrogen peroxide and was debrided of exudate and necrotic tissue within the affected areas. The burned area was then washed with lukewarm water and was thoroughly dried prior to application of the topical ointment composition of Example III. The relief felt by the patient was almost immediate. The wound was redressed each 12 hours and it was noticed that with each subsequent redressing of the wound the affected areas became easier to clean and the ointment which had been previously applied to the affected areas did not adhere in any way. By the third day, the wounds appeared clean and small patches of newly formed tissue could be seen. At this time the topical ointment composition of Example II was used and the affected area was cleansed prior to each application with the dispersion of antacids described in Example III instead of the warm hydrogen peroxide solution. A clean sterile gauze dressing was applied after each subsequent ointment application. The healing was pronounced. The small patches of skin seen after the third treatment began to grow and coalesce forming new skin virtually in the absence of scar tissue. After two weeks of treatment only a small area remained to be healed and complete closure of all other previously raw areas was apparent. The skin at the circumference of each raw area grew toward the center of the wound in the same manner as was noticed in Example II above involving the treatment of the decubitus ulcer.

EXAMPLE IX

In this instance a patient suffering from digital eczema, with no improvement after one month of treatment, was treated for three weeks with the topical ointment composition of Example II after which it was noted that complete healing and restoration of the epidermis in the previously affected area had occurred.

The present invention deals with the formulation of an ointment composition for topical application having the ability to bring the acid-base balance of the skin to a point where healing from within can take place. It has been shown, supra, that the topical ointment of the instant invention can be used for virtually any skin irritation, whether minor or severe, and apparently provides treatment by adjusting the pH of the affected area to a point where normal healthy tissue can be formed.

To achieve these properties a carefully balanced formulation of non-systemic hydroxides of magnesium and aluminum and a carbonate of calcium is provided in an aqueous suspension having a pH of approximately 8 to approximately 10. The aqueous suspension is then combined with an anhydrous lanolin based carrier material and a hydrophilic ointment based carrier material. The composition also may contain dibucaine hydrochloride which functions as a topical anesthetic and reduces the attendant discomfort.

In the antacid combination containing calcium carbonate, magnesium hydroxide and aluminum hydroxide, the calcium carbonate is included for its rapid neutralizing power and length of neutralization. The aluminum hydroxide acts as a buffering antacid producing a slower neutralization reaction and this compound also exhibits an astringent quality. The magnesium hydroxide provides antacid properties and also provides the ointment with a smooth, soothing texture which is pleasing to the skin along with cleansing properties.

I claim:

1. A topical ointment composition consisting essentially of an admixture of:
   a. a mixture of non-systemic bases consisting of from about 7 to about 82 weight percent calcium carbonate, from about 5 to about 77 weight percent magnesium hydroxide and from about 6 to about 80 weight percent aluminum hydroxide, with the proviso that the percentages of said components in said mixture total 100% thereof; and
   b. a mixture of carrier materials consisting essentially of anhydrous lanolin and hydrophilic ointment said carrier materials being present in said carrier mixture in a weight ratio of approximately 2:1 to 1:2; said ointment containing a weight ratio of said mixture of 1:21 to 1 to 213, effective to promote growth of normal healthy body tissues.

2. A topical ointment composition as set forth in claim 1 further containing an effective amount of a topical anesthetic.

3. The topical ointment composition as set forth in claim 1 wherein said mixture of bases consists of about 25 to about 50 weight percent of each of said components.

4. The topical ointment composition as set forth in claim 3 wherein said mixture of bases consists of about 37 weight percent calcium carbonate, about 29.7 weight percent magnesium hydroxide and about 33.3 weight percent of aluminum hydroxide.

5. The topical ointment composition as set forth in claim 4 wherein said carrier mixture materials are in substantially equal quantities.

6. A topical ointment composition consisting essentially of an admixture of:
   a. a paste comprising a mixture of non-systemic bases consisting of from about 7 to about 82 weight percent calcium carbonate, from about 5 to about 77 weight percent magnesium hydroxide and from about 6 to about 80 weight percent aluminum hydroxide, with the proviso that the percentages of said components in said mixture total 100% thereof, and a sufficient amount of water to present a smooth, moist paste; and
   b. a mixture of carrier materials consisting essentially of anhydrous lanolin and hydrophilic ointment, said carrier materials being present in said carrier mixture in a relative weight ratio of approximately 2:1 to 1:2; said ointment containing a weight ratio of said mixture of bases to carrier of 1:21 to 1:213 effective to promote growth of normal healthy body tissue.

7. The topical ointment composition as set forth in claim 6 wherein said paste has a pH of from about 8 to about 9.5.

8. The topical ointment composition as set forth in claim 6 wherein said mixture of bases consists of about 25 to about 50 weight percent of each of said components.

9. The topical ointment composition as set forth in claim 8 wherein said mixture of bases consists of about 37 weight percent calcium carbonate, about 29.7 weight percent magnesium hydroxide and about 33.3 weight percent aluminum hydroxide.

10. The topical ointment composition as set forth in claim 9 wherein said carrier materials are in substantially equal quantities.

11. A topical ointment composition as set forth in claim 6 further containing an effective amount of a topical anesthetic.

12. A topical ointment composition as set forth in claim 10 further containing an effective amount of a topical anesthetic.

13. The topical ointment composition as set forth in claim 6 consisting of: calcium carbonate, 250 parts by weight; magnesium hydroxide, 200 parts by weight; aluminum hydroxide, 225 parts by weight; dibucaine hydrochloride, 100 parts by weight; anhydrous lanolin, 28,350 parts by weight; and hydrophilic ointment, 28,350 parts by weight.

* * * * *